United States Patent
Vedula et al.

(10) Patent No.: US 7,405,402 B1
(45) Date of Patent: Jul. 29, 2008

(54) METHOD AND APPARATUS FOR ABERRATION-INSENSITIVE ELECTRON BEAM IMAGING

(75) Inventors: Srinivas Vedula, Fremont, CA (US);
Amir Azordegan, Santa Clara, CA (US);
Laurence Hordon, Santa Clara, CA (US); Alan D. Brodie, Palo Alto, CA (US); Gian Francesco Lorusso, Leuveen (BE); Takuji Tada, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 232 days.

(21) Appl. No.: 11/360,930

(22) Filed: Feb. 22, 2006

Related U.S. Application Data

(60) Provisional application No. 60/775,145, filed on Feb. 21, 2006.

(51) Int. Cl.
*G01N 23/00* (2006.01)
*G21K 7/00* (2006.01)
*H01J 3/14* (2006.01)

(52) U.S. Cl. .............. 250/310; 250/306; 250/307; 250/311; 250/396 R; 250/492.3

(58) Field of Classification Search ........... 250/306, 250/307, 309–311, 396 ML, 396 R, 397–399, 250/492.1, 492.2, 492.22, 492.23, 492.3
See application file for complete search history.

(56) References Cited

U.S. PATENT DOCUMENTS

| | | | | |
|---|---|---|---|---|
| 5,633,507 A * | 5/1997 | Pfeiffer et al. | ......... | 250/492.23 |
| 5,644,132 A * | 7/1997 | Litman et al. | ......... | 250/310 |
| 5,994,708 A * | 11/1999 | Nakasuji | ......... | 250/492.23 |
| 6,069,684 A * | 5/2000 | Golladay et al. | ......... | 355/53 |
| 6,417,516 B1 * | 7/2002 | Nakajima | ......... | 250/492.3 |
| 6,774,361 B2 * | 8/2004 | Bawendi et al. | ......... | 250/307 |
| 6,836,373 B2 | 12/2004 | Hosokawa | | |
| 6,858,843 B1 | 2/2005 | Mankos et al. | | |
| 6,858,844 B2 | 2/2005 | Zach | | |
| 6,861,651 B2 | 3/2005 | Rose | | |
| 6,885,001 B2 | 4/2005 | Ose et al. | | |
| 6,897,450 B2 | 5/2005 | Yonezawa | | |
| 6,946,654 B2 | 9/2005 | Gerlach et al. | | |
| 6,960,763 B2 | 11/2005 | Lopez et al. | | |
| 6,982,427 B2 | 1/2006 | Kawasaki et al. | | |
| 7,012,251 B2 | 3/2006 | Nakasuji et al. | | |
| 7,041,988 B2 | 5/2006 | Hamaguchi et al. | | |
| 7,098,468 B2 * | 8/2006 | Aloni et al. | ......... | 250/492.22 |
| 7,135,676 B2 * | 11/2006 | Nakasuji et al. | ......... | 250/310 |
| 7,157,703 B2 * | 1/2007 | Nakasuji et al. | ......... | 250/311 |
| 7,175,940 B2 * | 2/2007 | Laidig et al. | ......... | 430/5 |
| 7,250,618 B2 * | 7/2007 | Sogard et al. | ......... | 250/492.24 |
| 2002/0033449 A1 * | 3/2002 | Nakasuji et al. | ......... | 250/306 |

(Continued)

*Primary Examiner*—Bernard E Souw
(74) *Attorney, Agent, or Firm*—Okamoto & Benedicto LLP

(57) ABSTRACT

One embodiment relates to an electron beam apparatus for automated imaging of a substrate surface. An electron source is configured to emit electrons, and a gun lens is configured to focus the electrons emitted by the electron source so as to form an electron beam. A condenser lens system is configured to receive the electron beam and to reduce its numerical aperture to an ultra-low numerical aperture. An objective lens is configured to focus the ultra-low numerical aperture beam onto the substrate surface. Other embodiments are also disclosed.

20 Claims, 8 Drawing Sheets

U.S. PATENT DOCUMENTS

| | | | |
|---|---|---|---|
| 2002/0074506 A1* | 6/2002 | Gordon et al. | 250/398 |
| 2002/0142496 A1* | 10/2002 | Nakasuji et al. | 438/14 |
| 2002/0179845 A1* | 12/2002 | Kienzle | 250/396 R |
| 2003/0206283 A1* | 11/2003 | de Jager et al. | 355/67 |
| 2003/0207475 A1* | 11/2003 | Nakasuji et al. | 438/14 |
| 2003/0209676 A1* | 11/2003 | Loschner et al. | 250/492.2 |
| 2005/0045821 A1* | 3/2005 | Noji et al. | 250/311 |
| 2005/0263715 A1* | 12/2005 | Nakasuji et al. | 250/396 ML |
| 2005/0274911 A1* | 12/2005 | Aloni et al. | 250/492.22 |
| 2006/0169900 A1* | 8/2006 | Noji et al. | 250/310 |
| 2006/0243918 A1* | 11/2006 | Aloni et al. | 250/492.2 |
| 2006/0243922 A1* | 11/2006 | Aloni et al. | 250/492.22 |
| 2006/0255269 A1* | 11/2006 | Kawasaki et al. | 250/310 |
| 2007/0057186 A1* | 3/2007 | Nakasuji et al. | 250/310 |
| 2008/0042060 A1* | 2/2008 | Nakasuji et al. | 250/310 |

* cited by examiner

Conventional
502

NA = 20 mrad

Aberration-
Insensitive
504

NA < 5 mrad

Conventional
602

NA = 8 mRad

Aberration-
Insensitive
604

Ultra-low NA
(NA < 5 mRad)

METHOD AND APPARATUS FOR ABERRATION-INSENSITIVE ELECTRON BEAM IMAGING

CROSS-REFERENCE TO RELATED APPLICATION

This application claims the benefit of U.S. Provisional Application No. 60/775,145 entitled "Method and Apparatus for Aberration-Insensitive Electron Beam Imaging," filed Feb. 21, 2006, by inventors Srinivas Vedula, Amir Azordegan, Laurence Hordon, Alan D. Brodie, Gian F. Lorusso and Takuji Tada.

BACKGROUND OF THE INVENTION

1. Field of the Invention

The present disclosure relates to electron beam (e-beam) apparatus and methods of operating same. More particularly, the present disclosure pertains to e-beam apparatus for automated measurement systems and automated inspection/review systems.

2. Description of the Background Art

Substrates, such as low-k dielectric and similar wafers, frequently have embedded charges. These embedded charges may cause beam aberration issues in electron beam imaging of such substrates. Such beam aberration issues may include, for example, astigmatism and/or defocusing.

Correcting for such beam aberrations is often a time consuming procedure for automated measurement systems and automated inspection/review systems. Conventional techniques to correct for beam aberrations typically involve adjustments to the strengths of octupole and/or quadrupole electron lenses in the e-beam column hardware. Such conventional beam aberration correction is a relatively slow process and requires additional beam dosage to the substrate which may result in damage to the specimen.

Furthermore, the conventional techniques for beam aberration correction may be limited by the adjustability of the octupole/quadrupole lenses and by other limitations of the e-beam column. Hence, only small amounts of beam aberration are usually correctable with the conventional techniques. In the event of extreme aberrations, the ranges of the adjustable column components typically reach a maximum ("max out"), leading to a failure to correct the high level of aberration.

The present disclosure describes a novel and inventive technique to reduce or eliminate the need for conventional beam aberration correction in certain applications.

SUMMARY

One embodiment relates to an electron beam apparatus configured for aberration-insensitive imaging of a substrate surface. An electron source is configured to emit electrons, and a gun lens is configured to focus the electrons so as to form an electron beam. A condenser lens system is configured to receive the electron beam and to reduce its numerical aperture to an ultra-low numerical aperture. An objective lens is configured to focus the ultra-low numerical aperture beam onto the substrate surface.

Another embodiment relates to a method of aberration-insensitive electron beam imaging of a substrate surface. Electrons are emitted from an electron source, and the electrons are focused by a gun lens so as to form an electron beam. The numerical aperture of the electron beam is reduced by a condenser lens system to an ultra-low numerical aperture. The ultra-low numerical aperture beam is focused onto the substrate surface by an objective lens.

Another embodiment relates to an apparatus configured for aberration-insensitive electron beam imaging of a substrate surface. The apparatus includes: means for emitting electrons; means for focusing the electrons emitted by the electron source so as to form an electron beam; electron lenses configured to reduce the numerical aperture of the beam to achieve an ultra-low numerical aperture beam; and means for focusing the ultra low numerical aperture beam onto the substrate surface.

Other embodiments are also disclosed.

These drawings are used to facilitate the explanation of embodiments of the present invention. The drawings are not necessarily to scale.

DETAILED DESCRIPTION

The present disclosure describes a novel and inventive technique which provides a mechanism to effectively "see through" beam aberrations caused by local charging effects on low-k dielectric and other semiconductor materials. The "see-through" mechanism is achieved by forming an ultra low numerical aperture (i.e. a "pencil-like") electron beam for imaging the substrate surface.

This technique advantageously eliminates the need for an additional beam aberration correction step in certain applications, such as automated critical dimension measurements and automated inspection or review. This enables a higher throughput for such automated instruments.

In addition, the presently-disclosed technique may be further useful in achieving an e-beam imaging focus which is insensitive to local charging across a substrate. For example, a few tens of volts of focus variation may exist due to local charging across a low-k dielectric wafer or other semiconductor substrate. Using the presently-disclosed technique, the entire wafer may be imaged without adjusting or changing the focus of the beam. This allows for a high throughput solution for surface image data collection in metrology and inspection or review applications for semiconductor manufacturing.

Figure 1A:
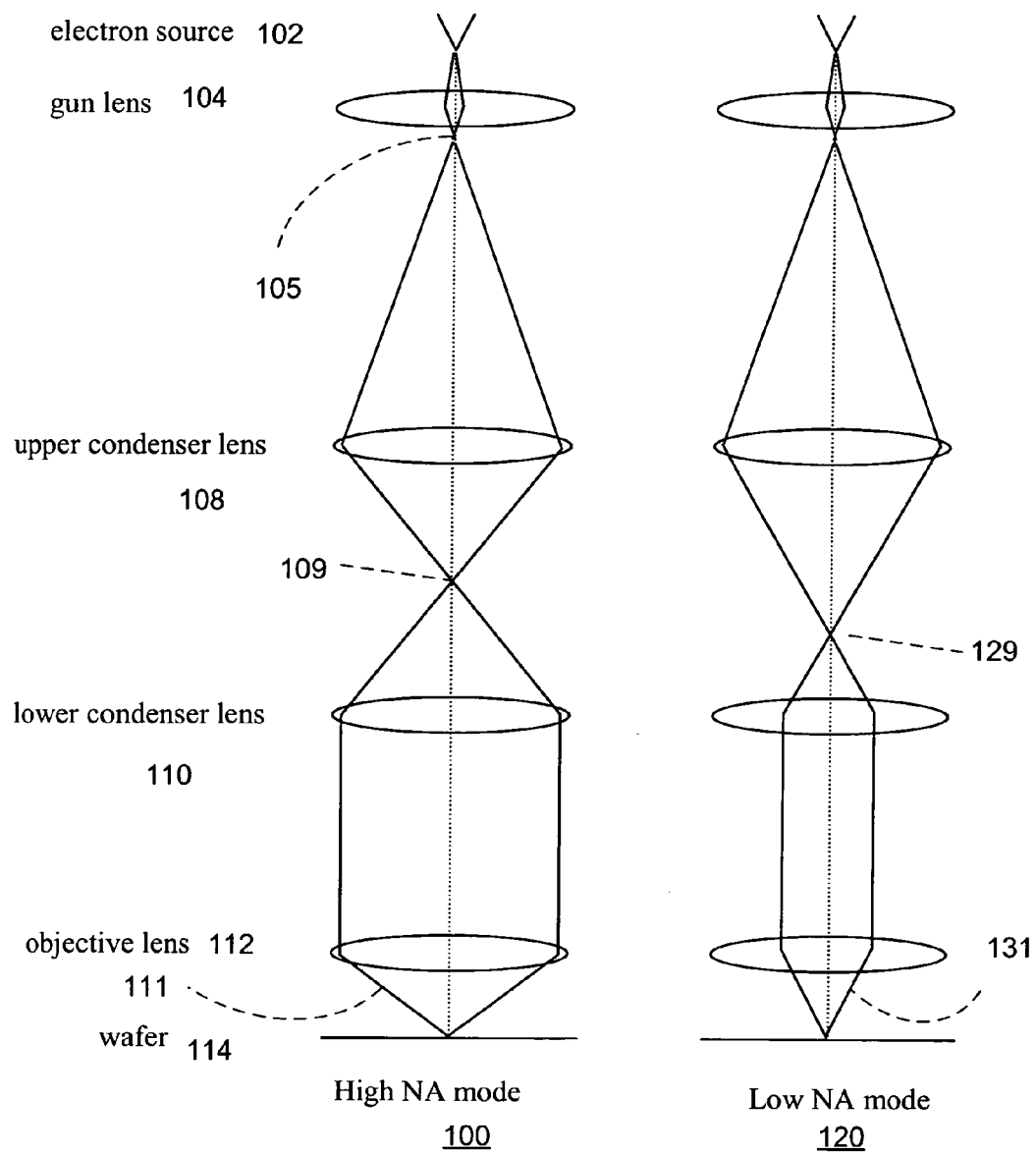
FIGS. 1A and 1B are schematic diagrams of an electron beam apparatus configured for conventional imaging (FIG. 1A) and for aberration-insensitive imaging (FIG. 1B) in accordance with an embodiment of the invention.
Figure 1B:
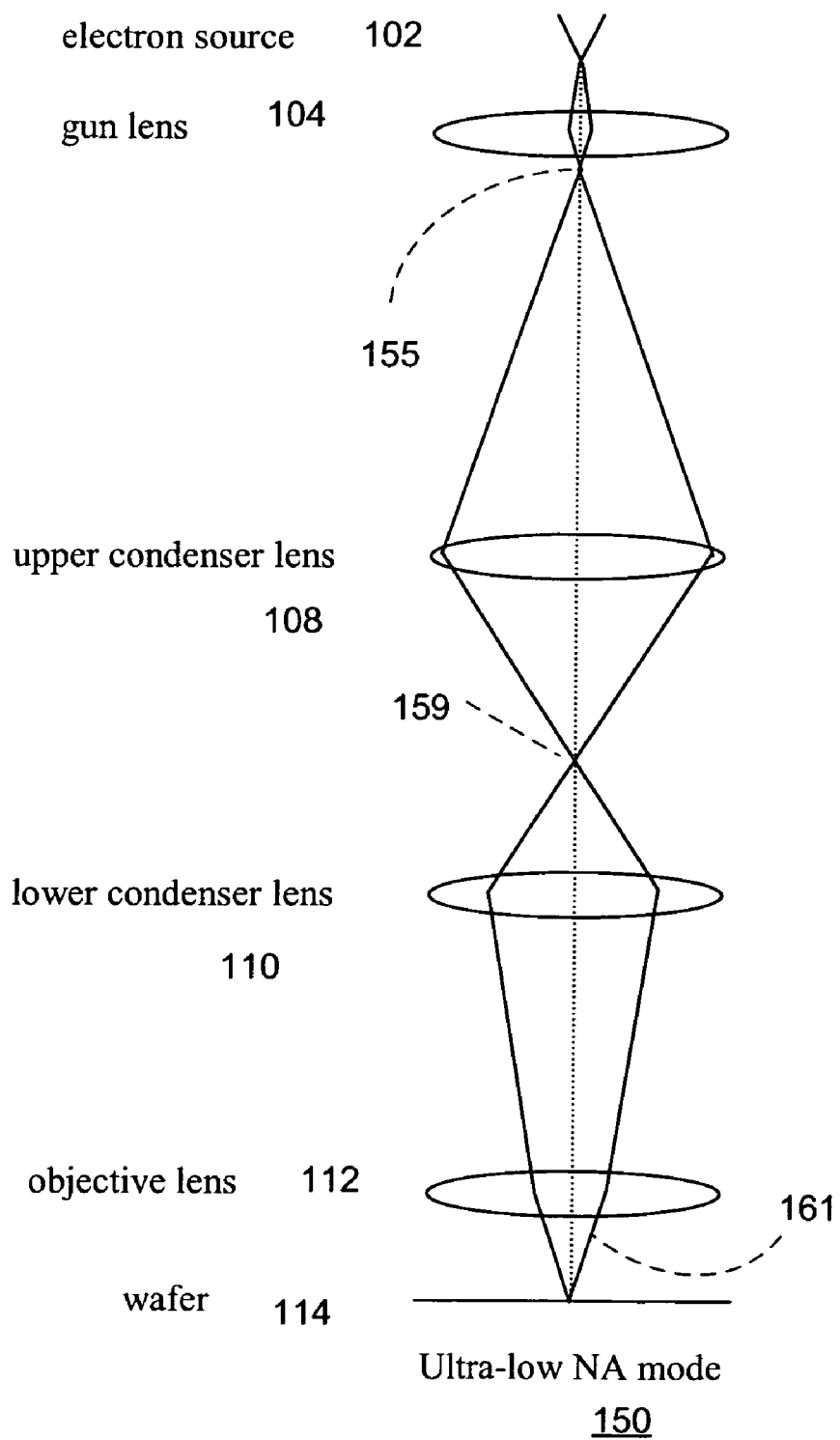

FIGS. 1A and 1B are schematic diagrams of an electron beam apparatus configured for conventional imaging (FIG. 1A) and for astigmatism-insensitive imaging (FIG. 1B) in accordance with an embodiment of the invention. In particular, FIG. 1A shows two conventional configurations, a first configuration for a high numerical aperture (NA) mode 100 and a second configuration for a low NA mode 120. FIG. 1B shows a third configuration for an ultra low NA mode 150. These images are not necessarily to scale, but they serve to illustrate the qualitative differences of the ultra low NA mode 150.

As shown in FIG. 1A, an electron source 102 emits electrons for forming a primary (imaging) electron beam. The electrons are focused into a beam by the gun lens 104, and the beam continues down the column structure of the apparatus. The diagram of FIG. 1A illustrates a rough "envelope" of the beam as it travels down the column. For example, a cross-over point 105 of the beam is shown below the gun lens 104.

Conventional electron beam columns often have a single condenser lens. However, as shown, there are at least two condenser lenses (108 and 110) in the apparatus in accordance with an embodiment of the invention. As discussed further below in relation to FIG. 1B, the multiple condenser lenses are used to create an ultra-low numerical aperture (ultra-low NA) beam 161 so as to achieve astigmatism-insensitive imaging In the configuration shown on the left side of FIG. 1A, the condenser lens system is configured to create a conventional high NA beam 111 for imaging at a high resolution. The condenser lens system may include, for example, multiple condenser electron lenses. For example, in the case of a condenser lens system with two condenser lenses 108 and 110, the upper condenser lens 108 may be set at a strength such that a beam crossover 109 exists roughly in the middle region between the upper condenser lens 108 and the lower condenser lens 110. The lower condenser lens 110 and the objective lens 112 may be set at strengths such that the beam 111 impinging upon the substrate 114 has a relatively high numerical aperture (NA). A high NA may be above 20 mRad. Such a high NA beam may be used for high-resolution imaging. In this mode, high resolution images are obtainable with the proper focus.

In the configuration shown on the right side of FIG. 1A, the condenser lens system is configured to create a conventional low NA beam 120. The condenser lens system may include, for example, multiple condenser electron lenses. For example, in the case of a condenser lens system with two condenser lenses 108 and 110, the upper condenser lens 108 may be set at a strength such that a beam crossover 129 exists closer to the lower condenser lens 110. The lower condenser lens 110 and the objective lens 112 may be set at strengths such that the beam 131 impinging upon the substrate 114 has a relatively low numerical aperture (NA). A low NA may be below 20 mRad but above 5 mRad.

Similarly, as shown in FIG. 1B, the electron source 152 emits electrons for forming a primary (imaging) electron beam. The electrons are focused into a beam by the gun lens 104, and the beam continues down the column structure of the apparatus. The diagram of FIG. 1B illustrates a rough "envelope" of the beam as it travels down the column. For example, a cross-over point 155 of the beam is shown below the gun lens 104.

In the configuration of FIG. 1B, the condenser lens system is configured to create an ultra low NA beam 161 for imaging at a high depth of field (DOF). For example, in the case of a condenser lens system with two condenser lenses 108 and 110, the upper condenser lens 108 may be set at a strength such that a beam crossover 159 exists approximately as shown in the region between the condenser lenses. The lower condenser lens 110 and the objective lens 112 may be set at a strength such that the beam 161 impinging upon the substrate 114 has an ultra low numerical aperture (NA). An ultra low NA is defined herein as a NA of five milliradians (5 mRad) or less. In this mode, imaging may be performed which "sees through" the beam aberrations that may affect imaging in the conventional high-resolution mode.

Advantageously, this configuration 150 allows for high-throughput imaging as the beam aberration correction step may be skipped. Furthermore, the additional dosage imposed upon a substrate during such beam aberration correction is also avoided. In cases where large beam aberrations may be uncorrectable in conventional imaging, this technique enables the obtaining of an image undistorted by the aberrations. The trade-off of this technique is that the resolution of the imaging is slightly reduced.

Figure 2:
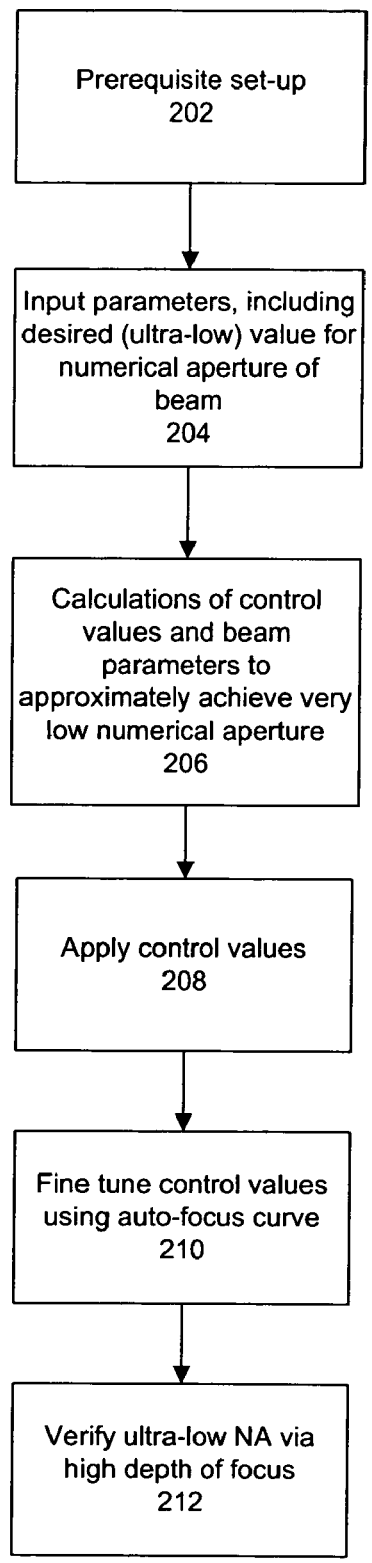
FIG. 2 is a flow chart depicting a method of aberration-insensitive electron beam imaging in accordance with an embodiment of the invention.

FIG. 2 is a flow chart depicting a method 200 of astigmatism-insensitive electron beam imaging in accordance with an embodiment of the invention.

Pre-requisite set-up 202 of the apparatus may be performed. The pre-requisite set-up may include, for example, the following. The electron gun may be mechanically aligned and turned on so as to be generating the electron beam. All lenses of the apparatus may be turned on. A special substrate sample may be loaded into the apparatus, and an e-beam image of the special sample may be generated such that a recognizable image appears on a display screen of the apparatus. Standard column alignment procedures may be performed. Other pre-requisite set-up steps may also be performed, depending upon the particular e-beam apparatus.

Parameters for the beam aberration imaging are input 204 via the user interface of the apparatus. The parameters may include, for example, the following.

(a) The landing energy for the electron beam may be input.

(b) The probe current for the electron beam may also be input.

(c) The extraction field may also be input based on the specific application.

(d) Finally, the desired low value for the numerical aperture (NA) for the imaging mode may also be set. For example, an ultra low NA value may be set which is 5 milli-radians (mRad) or less.

Various calculations may then be performed 206. These calculations determine control values and beam parameters which may be used to approximately achieve the desired low NA value. In one embodiment, one or more look-up tables (LUTs) may be used to implement these calculations. Linear interpolation may be used to obtain values in between values in the LUTs.

The calculations or determinations may include, for example, the following control values and beam parameters:

(i) the wafer bias voltage;

(ii) the objective lens voltage;

(iii) the focal length of the objective lens/wafer combination; (iv) the gun lens voltage; (v) beam crossover positions; (vi) control voltages for the condenser lens system; (vii) the objective lens currents; and (viii) other control values and beam parameters.

Once all the beam parameters and control values are calculated (for example, as discussed above), the control values may be applied 208 to the e-beam column hardware. A coarse beam alignment may then be performed.

In accordance with an embodiment of the present invention, subsequent fine tuning of the ultra low NA beam may then be performed. Such fine tuning steps are not performed in the conventional technique.

Figure 7A:
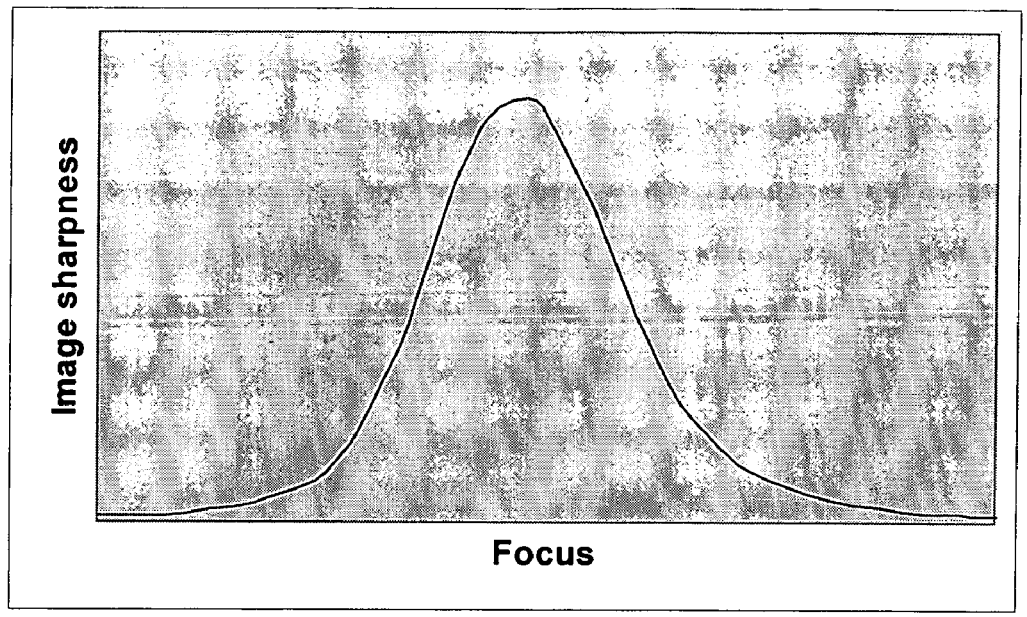
FIGS. 7A and 7B show auto focus curves under typical high-resolution imaging conditions (FIG. 7A) and under aberration-insensitive imaging conditions (FIG. 7B) in accordance with an embodiment of the invention.
Figure 7B:
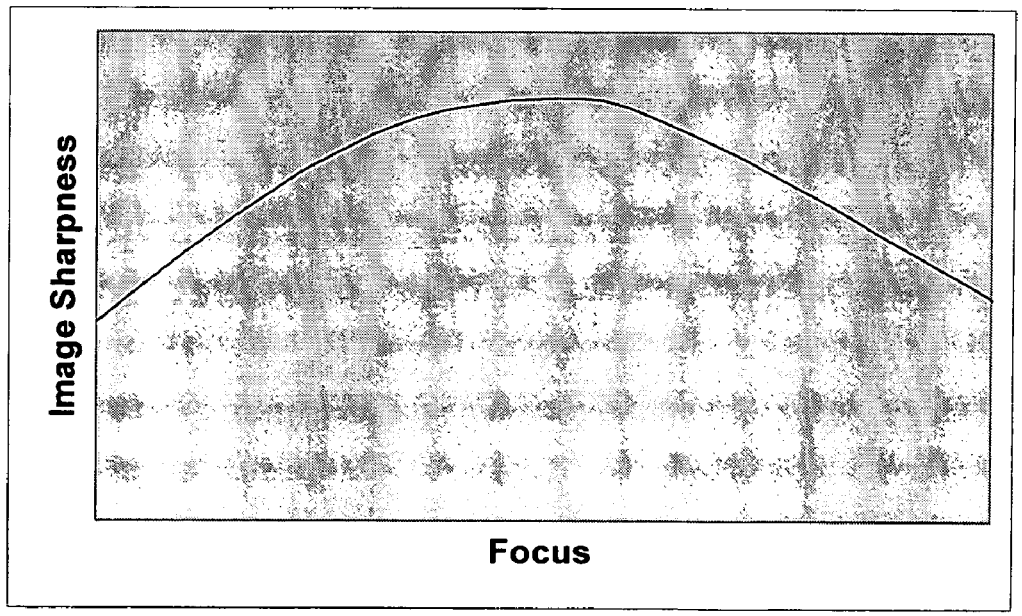

After application 208 of the control values as discussed above, the control values may be first fine tuned using an auto-focus curve 210. FIGS. 7A and 7B show illustrative auto-curves for a conventional beam (FIG. 7A) and for an ultra-low NA beam (FIG. 7B). In this case, the control values are fine tuned with an aim of achieving an auto focus curve closer to FIG. 7B than FIG. 7A.

In accordance with a specific implementation, the following steps may then be performed for up to several iterations: fine focus with the magnetic lens; beam align through the final lens; and stigmation correction.

Figure 3:
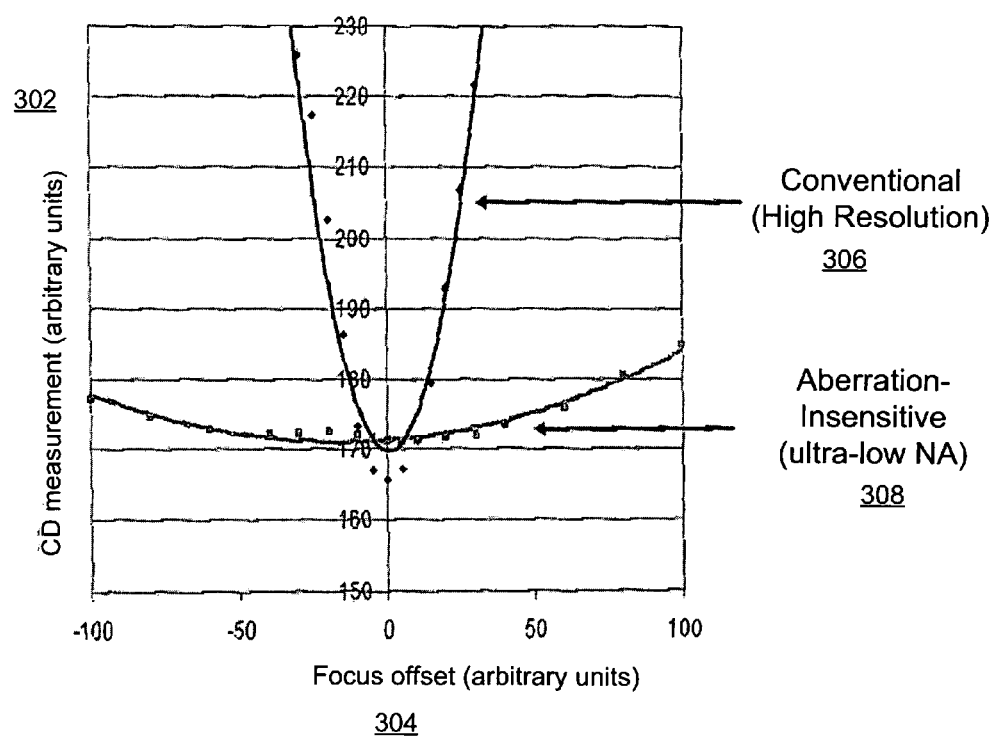
FIG. 3 is a graph showing critical dimension measurements versus focus offset for conventional high-resolution imaging and for aberration-insensitive imaging in accordance with an embodiment of the invention.

Thereafter, the ultra-low NA of the beam may be verified 212. The verification may be performed, for example, by measuring a critical dimension over a focus range so as to confirm the expected high depth of focus. A graph showing such measurements is shown in FIG. 3 and discussed below in relation thereto. Alternatively or additionally, the verification may be performed by obtaining image data of an appropriate feature over a focus range.

FIG. 3 is a graph showing critical dimension (CD) measurements 302 versus focus offset 304 for conventional high-resolution imaging and for aberration-insensitive imaging in accordance with an embodiment of the invention. The graph shows two sets of CD measurements.

A first set of data shows the conventional high-resolution imaging condition 306 of the e-beam apparatus. Under this conventional high-resolution imaging condition 306, the CD measurement 302 varies substantially with different focus strengths.

A second set of data shows the astigmatism-insensitive (i.e. high depth of field) imaging condition 308 of the e-beam apparatus in accordance with an embodiment of the invention. Under this aberration-insensitive imaging condition 308, the CD measurement 302 stays relatively flat with different focus strengths, evidencing a high depth of focus. Obtaining data which resembles the second set of data may be used to verify 212 that the e-beam apparatus is properly configured with an ultra low NA beam in accordance with the method 200 of FIG. 2.

Figure 4:
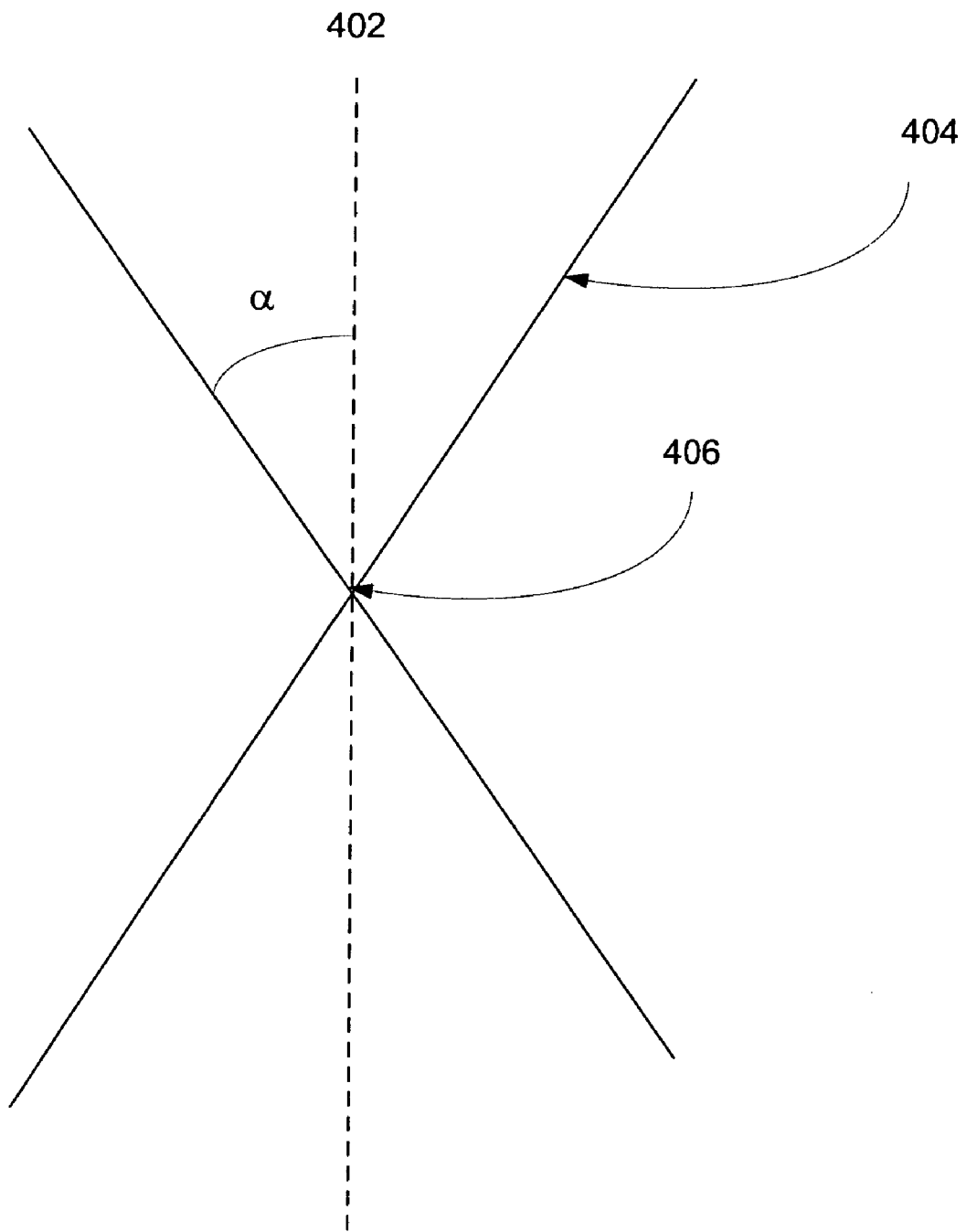
FIG. 4 is a diagram illustrating a numerical aperture of a beam.

FIG. 4 is a diagram illustrating a numerical aperture of an electron beam. The optical axis of the electron beam column 402 is shown. The beam cone 404 and a beam crossover 406 are depicted. The angle α shown corresponds the numerical aperture of the beam.

Figure 5A:
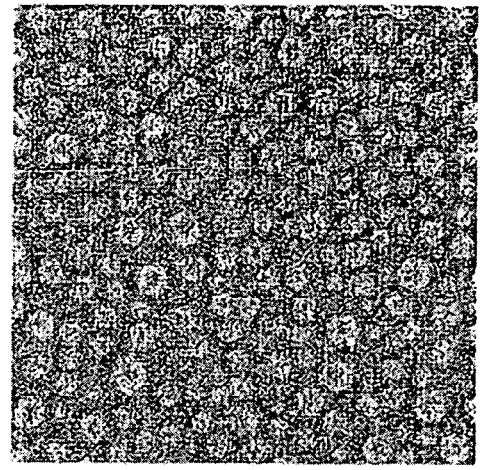
FIG. 5A shows an e-beam image of a surface area of a substrate under conventional high-resolution imaging conditions.

FIG. 5A shows an e-beam image 502 of a surface area of a sample under conventional high-resolution imaging conditions. The sample is a standard resolution sample with tin spheres sputtered on graphite. Here, the field of view is 375 nm, and the beam has a numerical aperture of 20 mRad. As shown, the image is sharp in such a conventional high-resolution image.

Figure 5B:
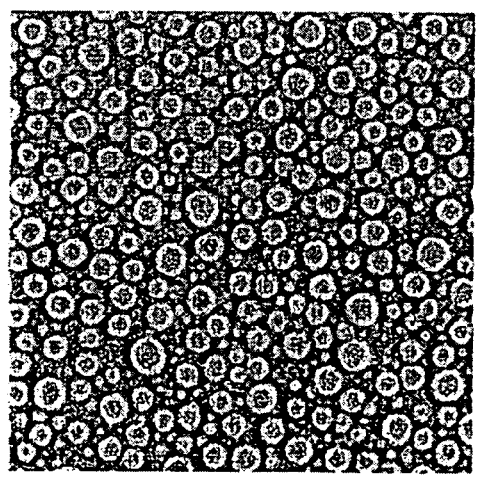
FIG. 5B shows an e-beam image of a surface area of a substrate under aberration-insensitive imaging conditions in accordance with an embodiment of the invention.

FIG. 5B shows an e-beam image 504 of a surface area of the standard resolution sample (tin spheres sputtered on graphite) under aberration-insensitive imaging conditions in accordance with an embodiment of the invention. In this example, the field of view is 375 nm, and the beam has an ultra-low NA (i.e., NA<5 mRad). As shown, the image of the tin spheres is slightly less sharp in such an aberration-insensitive image.

Though less sharp, such an e-beam image 504 is also less sensitive to variation in beam aberration, and hence may be advantageously used, for example, on wafers that exhibit severe astigmatism, or on wafers that exhibit large focus variation across the wafer. Such an aberration-insensitive imaging mode may be utilized to perform automated metrology or automated inspection or automated review without having to focus the image at each site on the substrate, thus substantially increasing the throughput of the automated instrumentation.

Figure 6A:
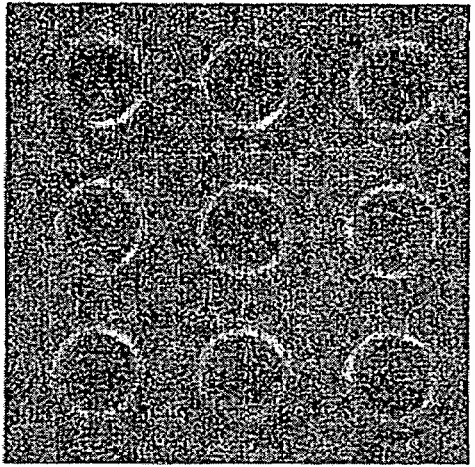
FIG. 6A shows an e-beam image of scribe line features on a wafer under conventional high-resolution imaging conditions.

FIG. 6A shows an e-beam image 602 of scribe line features near a center of a wafer under conventional high-resolution imaging conditions. In this example, the conventional imaging conditions result in a numerical aperture (NA) of about 8 mRad. As shown, the image exhibits substantial distortion due to astigmatism in such a conventional high-resolution image.

Figure 6B:
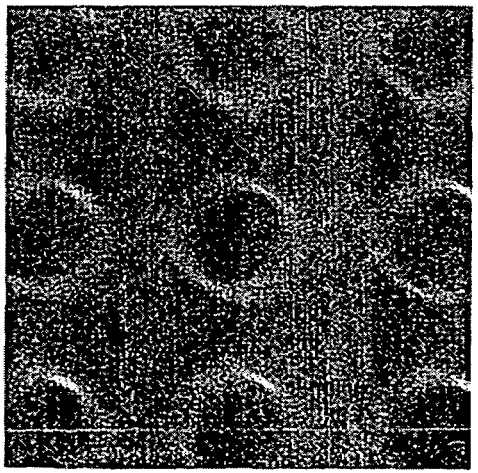
FIG. 6B shows an e-beam image of scribe line features on a wafer under aberration-insensitive imaging conditions in accordance with an embodiment of the invention.

FIG. 6B shows an e-beam image 604 of scribe line features near a center of a wafer under aberration-insensitive imaging conditions in accordance with an embodiment of the invention. Under such conditions as discussed above, the NA of the beam is ultra low (<5 mRad).

As disclosed herein, such an e-beam image 604 is substantially insensitive to aberrations, including astigmatism. Such an aberration-insensitive imaging mode may be utilized to perform automated metrology or automated inspection/review without having to focus the image at each site on the substrate, thus substantially increasing the throughput of the automated instrumentation.

In addition, the technique disclosed herein advantageously allows measurement of the surface voltage at a measurement site without need to measure (map) at multiple sites (which would be slow). Also, there is no need to interpolate between the sites (which may introduce inaccuracies).

In addition, the technique disclosed herein advantageously adapts to, or is substantially insensitive to, local changes in landing energy. This improves metrology accuracy.

Furthermore, the technique disclosed herein is advantageously robust due to its not needing an image pattern for focusing. Focusing may be performed on a bare wafer using this technique.

Moreover, the technique disclosed herein is advantageously less destructive because it can be performed at very low energy densities (i.e. at low magnification). This leads to much less wafer dosing, and hence to less wafer damage.

FIGS. 7A and 7B show auto focus curves under typical high-resolution imaging conditions (FIG. 7A) and under aberration-insensitive imaging conditions (FIG. 7B) in accordance with an embodiment of the invention. As seen from FIG. 7A, the image sharpness curve peaks over a relatively narrow range of focus offsets. In comparison, in FIG. 7B, the image sharpness curve has wide peak over a relatively large range of focus offsets.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam apparatus for automated imaging of a substrate surface, the apparatus comprising:
    an electron source configured to emit electrons;
    a gun lens configured to focus the electrons emitted by the electron source so as to form an electron beam;
    a condenser and objective lens system configured to receive the electron beam and to reduce a numerical aperture of the beam to an ultra-low numerical aperture, wherein aberration-insensitive imaging is performed without aberration correction.

2. The apparatus of claim 1, wherein the ultra-low numerical aperture beam has a numerical aperture of less than five milliradians (5 mRad).

3. The apparatus of claim 1, further comprising:
    processor-executable code configured to determine control values for the electron beam apparatus so as to achieve the beam with ultra-low numerical aperture.

4. The apparatus of claim 3, wherein the processor-executable code determines control values for at least two electron lenses in the condenser lens system.

5. The apparatus of claim 4, wherein the control values for the lenses in the condenser lens system are determined using a look-up table and interpolation.

6. The apparatus of claim 1, wherein the apparatus is further configured for high-resolution imaging of the substrate surface using an electron beam column which is separate from the electron source and lenses for the aberration-insensitive imaging.

7. The apparatus of claim 1, wherein the imaging of the surface is insensitive to surface charge variations.

8. The apparatus of claim 1, wherein the apparatus comprises a critical dimension secondary electron microscope (CD-SEM).

9. The apparatus of claim 1, wherein the apparatus comprises an automated inspection or review system.

10. A method of aberration-insensitive electron beam imaging of a substrate surface, the method comprising:
    emitting electrons from an electron source;
    focusing the electrons emitted by the electron source by a gun lens so as to form an electron beam;
    reducing a numerical aperture of the beam to an ultra-low numerical aperture by a condenser and objective lens system, wherein aberration-insensitive imaging is performed without aberration correction step.

11. The method of claim 10, wherein the ultra-low numerical aperture beam has a numerical aperture of less than five milliradians.

12. The method of claim 11, further comprising:
    using a look-up table and interpolation in determining control values and beam parameters and adjusting the control values using an auto-focus curve so as to achieve the ultra-low numerical aperture beam.

13. The method of claim 12 wherein the beam parameters include beam crossovers.

14. The method of claim 13, wherein based on the beam crossovers, control values for the condenser lens system are determined.

15. The method of claim 10, wherein the condenser lens system includes upper and lower condenser lenses.

16. The method of claim 10, further comprising:
    high-resolution imaging of the substrate surface using an electron beam column which is separate from the electron source and lenses for the aberration-insensitive imaging.

17. An apparatus configured for aberration-insensitive electron beam imaging of a substrate surface, the apparatus comprising:
    means for emitting electrons;
    means for focusing the electrons emitted by the electron source so as to form an electron beam;
    electron lenses configured to reduce a numerical aperture of the beam to an ultra low numerical aperture, wherein aberration-insensitive imaging is performed without aberration correction.

18. The apparatus of claim 17, wherein the low numerical aperture beam has a numerical aperture of less than five milli-radians.

19. The apparatus of claim 18, further comprising:
    at least one look-up table and means for interpolating for determining control values and beam parameters so as to achieve the beam with ultra low numerical aperture.

20. The apparatus of claim 19, wherein the beam parameters include crossover positions, and wherein based on the crossover positions, control values for the electron lenses are determined.

* * * * *